United States Patent [19]

Haarmann

[11] Patent Number: 4,842,513

[45] Date of Patent: Jun. 27, 1989

[54] ORTHODONTIC DEVICE

[75] Inventor: Bodo Haarmann, Bad Rothenfelde, Fed. Rep. of Germany

[73] Assignee: Harodent-KFO Dental-Vertrieb GmbH, Georgsmarienhuette, Fed. Rep. of Germany

[21] Appl. No.: 931,767

[22] Filed: Nov. 17, 1986

[30] Foreign Application Priority Data

Nov. 23, 1985 [DE] Fed. Rep. of Germany ....... 3541506

[51] Int. Cl.[4] ................................................ A61C 3/00
[52] U.S. Cl. ............................................. 433/9; 433/8
[58] Field of Search ...................... 433/8, 9, 10, 16, 23; 29/160.6

[56] References Cited

U.S. PATENT DOCUMENTS

| 2,045,025 | 6/1936 | Richardson | 433/8 |
|---|---|---|---|
| 3,075,287 | 1/1963 | Weinger | 433/16 |
| 4,068,379 | 1/1978 | Miller et al. | 433/9 |
| 4,322,206 | 3/1982 | Reynolds | 433/8 |
| 4,349,334 | 9/1982 | Webb et al. | 433/9 |
| 4,415,330 | 11/1983 | Daisley et al. | 433/16 |
| 4,529,382 | 7/1985 | Creekmore | 433/16 |
| 4,531,911 | 7/1985 | Creekmore | 433/9 |
| 4,536,154 | 8/1985 | Garton, Jr. et al. | 433/16 |
| 4,544,353 | 10/1985 | Maurer et al. | 433/9 |
| 4,595,598 | 6/1986 | DeLuca et al. | 433/9 |
| 4,614,497 | 9/1986 | Kurz | 433/10 |
| 4,659,309 | 4/1987 | Markel | 433/16 |

Primary Examiner—Gene Mancene
Assistant Examiner—Adriene J. Lepiane
Attorney, Agent, or Firm—Jordan and Hamburg

[57] ABSTRACT

An orthodontic device has the form of a bracket with wings which are disposed on a base plate and which are constructed in the form of separate shaped parts and welded onto the base plate, the base plate itself forming a separately preformed component. Preferably, the separately preformed base plate is constructed in the form of an adhesive support or adhesive base, and for this purpose is constructed with undercut recesses on the underside of the base plate.

13 Claims, 3 Drawing Sheets

ORTHODONTIC DEVICE

BACKGROUND OF THE INVENTION

The invention relates to an orthodontic device in the form of a bracket with wings disposed on a base plate.

German patent No. 27 16 341 describes a bracket of this type consisting of an integral part which is parted off from a wire strand preformed by form milling. Depending on the design of the brackets, finish-milling work is still necessary on the individual bracket after parting off from the wire strand, for example when the bracket slot is to be inclined.

After being manufactured, brackets of this type are provided at the underside of their base plate with a separate adhesive support or adhesive base which may consist of a layer of metal foil and a layer of metal gauze welded to the layer of metal foil. The layer of metal foil may, however, be welded directly to the underside of the base plate of the bracket.

Brackets of this type are extremely expensive, can only be produced in large numbers of uniform brackets in order to limit the production costs and, particularly if the bracket slot is inclined, have unequal thicknesses of material at each side of the bracket slot and hence regions of very different strength. The preprofiled wire strands as starting material for production lead to a severe limitation in shape while the separate adhesive support or adhesive base involves considerable additional costs and causes a spacing of the bracket from the tooth surface to which the bracket is to be stuck which is increased by the thickness of the adhesive base.

Brackets constructed in the form of integral parts are further known which are formed from an individually preformed cast blank for each bracket. The final shaping of such cast brackets, which again have to be provided with a separate adhesive support or adhesive base at the underside of their base plate, is effected by finish-milling the cast blanks introduced into pallets in groups. Such brackets are also extremely expensive because of their manufacture and suffer from the further disadvantages already listed above. Here, too, the casting mould predetermines a basic shape for the blank which only leaves strictly limited possibilities of modification during the production of the finished shape. Therefore, about 60 different casting moulds are needed in order to produce those blanks from which more than 100 different shapes of brackets are then completed.

SUMMARY OF THE INVENTION

It is an object of the present invention to provide an orthodontic device in the form of a bracket of the type mentioned at the beginning which can be produced particularly simply and therefore economically and which leaves a wide latitude in design.

According to the present invention, in an orthodontic device in the form of a bracket having wings disposed on a base plate the wings are constructed in the form of separate shaped parts and are welded onto the base plate, the base plate itself forming a separately preformed component.

The wings may be formed from shaped parts cut out individually, in their final shape, from a sheet bar by means of a laser cutting device.

The end faces of the wings may be rounded with an inward curvature and end in an acute-angled foot region and the wings may be welded to the base plate in their acute-angled foot regions.

Preferably, the wings and the base plate are connected to one another in fusion welding regions, e.g. spot regions, without welding flux and conveniently by a laser welding operation.

A further object of the present invention is to provide an orthodontic bracket which can be produced particularly simply and economically and which no longer needs any separate adhesive support or adhesive base.

To this end the present invention also provides a base plate for an orthodontic device wherein the base plate is itself directly constructed in the form of an adhesive support or adhesive base.

Thus the base plate may be provided with undercut recesses which are arranged distributed over its underside and are open towards its underside.

Preferably, the recesses have the shape of a circular cone, the apex of which is adjacent to the top of the base plate and the centre axis of which forms an acute angle of inclination with the underside of the base plate.

All the recesses may have uniform alignment or the recesses may be differently aligned in groups. Two or more recesses which are different from one another may be combined to form a group. The point of intersection of the centre axes of recesses which are different from one another may be in the plane of the underside of the base plate. Again, the point of intersection may be situated in the vicinity of the apices of the cones. Preferably the recesses are formed as laser beam bores.

The invention provides an orthodontic device with which the most varied formations of the bracket, such as are needed for the most varied dentofacial orthopaedic measures, can be brought about in a simple manner by combining and connecting preformed components. The base plate, which for its part forms a separately preformed component shaped specifically for the tooth may, by a pretreatment, be constructed directly as an adhesive support or adhesive base, so that a separate adhesive support and the connection of such an adhesive support to the base plate of a bracket is eliminated.

A base plate for an orthodontic device in accordance with the present invention may be used as a separate adhesive support or adhesive base for a conventional orthodontic bracket as well as for part of an orthodontic device according to the present invention.

Numerous further details and advantages will become apparent from the following description and the drawings in which various embodiments of the present invention are illustrated diagrammatically in more detail.

DETAILED DESCRIPTION OF THE PREFERRED EMBODIMENTS

Figure 1:
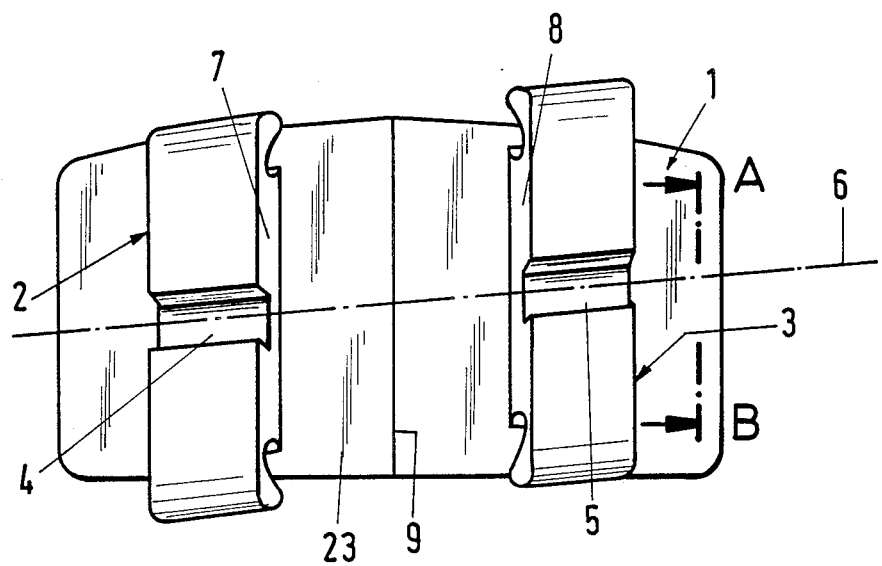
FIG. 1 shows a plan view of an orthodontic device according to the present invention with an angular bracket slot.

The orthodontic device in the form of a bracket, illustrated in FIG. 1, comprises a base plate 1 and wings 2, 3 disposed on the base plate. Like the wings 2, 3, the base plate 1 consists of metal, particularly stainless steel. The base plate 1 is a separately preformed component which can be shaped, for example curved, specifically for a tooth or teeth to be treated and which is cut out of a sheet bar or cut off from a strip and then trimmed and polished.

Welded onto the predetermined area of the curved top of the base plate 1 are the wings 2, 3, and in the bracket shown in FIG. 1, they have mutual parallel offsetting as a result of which an angled bracket slot is formed by the slots, 4, 5 of the wings 2, 3, the angulation of which is symbolized by the bracket-slot plane 6 shown in chain line. The boundary surfaces of the slots 4, 5 are aligned perpendicular to the longitudinal side faces 7 and 8 respectively of the wings so that angle bracket slots do not require any special shape of wing but can be produced by appropriate arrangement of the wings 2, 3 within the predetermined area of the curved top of their base plate 1.

Figure 2:
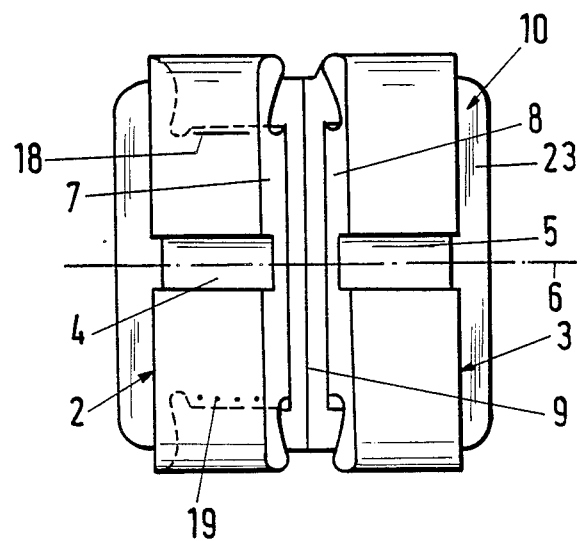
FIG. 2 shows a plan view of a device according to the present invention of a modified shape.
Figure 3:
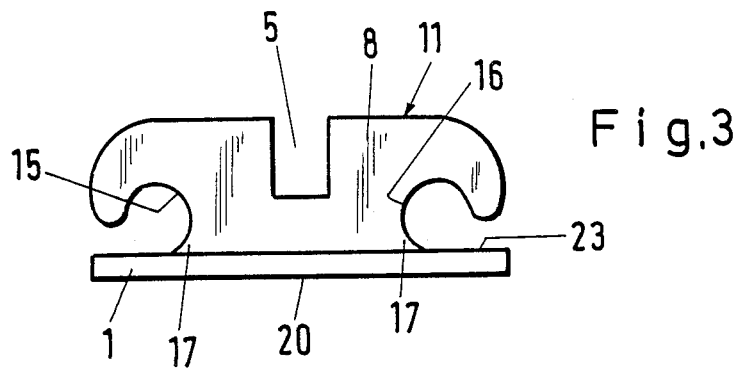
FIGS. 3 to 6 show views of various standard bracket sections viewed in a direction parallel to the bracket slot.
Figure 4:
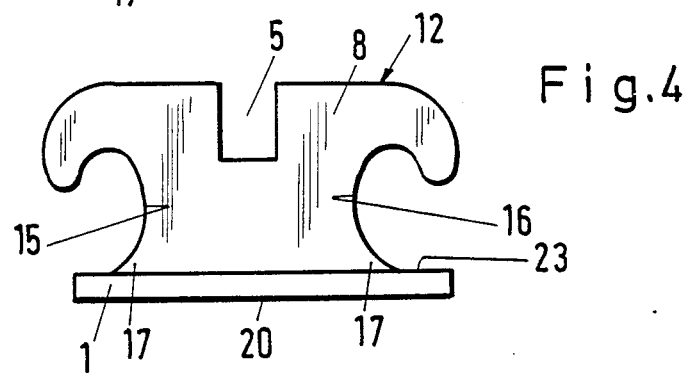
Figure 5:
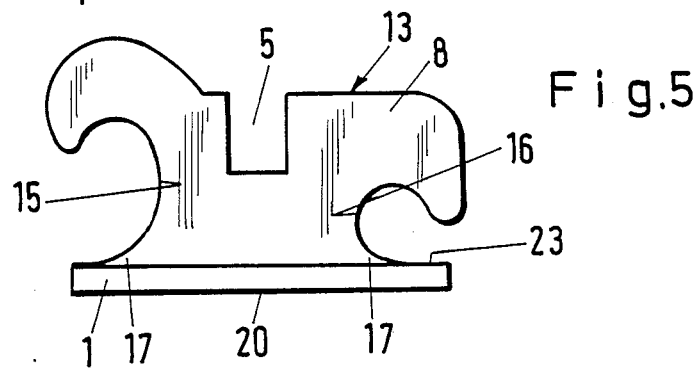
Figure 6:
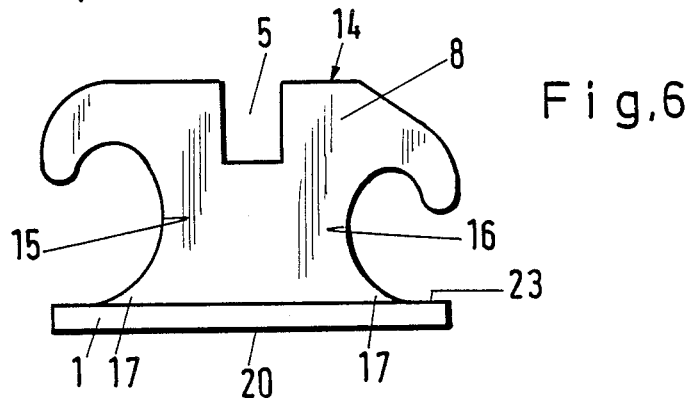

This is made clear by FIG. 2 in which the same wings 2, 3 are arranged on a base plate 10 of smaller predetermined top area in such a manner that the slot plane 6 extends perpendicular to the centre marking 9 of the base plate 10.

The wings 2, 3 like the wings, 11, 12, 13, 14 in FIGS. 3 to 6, are formed from shaped parts cut out individually, immediately in their final shape, from a sheet bar by means of a laser cutting device. After being cut out by the appropriately program-controlled laser cutting device, the shaped parts are merely trimmed and polished before they are then placed on their base plate 1 by a setting and holding device, to be subsequently connected to the base plate 1 by a welding operation, particularly a laser welding operation. The whole contour illustrated for different shapes in FIGS. 3 to 6 is formed by the cutting operation, the end faces 15, 16 of the wings 2, 3 or 11 to 14 being rounded with an inward curvature and each ending in an acute-angled foot region 17 in which or along which the welding to the base plate 1 or 10 is effected. The wings 2, 3 or 11 to 14 and the base plate 1 or 10 are preferably connected to one another in fusion welding regions without welding flux, which welding regions are symbolized in FIG. 2 for the wings 2 by the line 18 or the dots 19 respectively. The fusion welding regions are preferably formed by a laser welding operation which provides sharply contoured, particularly precise fusion welded joints. The shape and size of the fusion welding regions depends on the particular circumstances, and in individual cases a single fusion weld spot in the region of each end face 15, 16 may suffice for the production of a sufficiently firm connection.

Fundamentally, the base plate 1 or 10 can be provided with a separate adhesive support or adhesive base, such as is known for conventional brackets. Preferably, however, the base plate 1 or 10 is itself directly constructed in the form of an adhesive support or adhesive base and is provided for this purpose with undercut recesses 21 and/or 22 which are arranged distributed over its underside 20 and are open towards the underside 20. The recesses 21, 22 have the shape of a circular cone, the apex of which is adjacent to the top 23 of the base plate 1 or 10 and the centre axis of which forms an acute angle of inclination 24 or 25 with the underside 20 of the base plate 1 or 10. The size of the angle of inclination 24, 25 is preferably in the range from 40° to 60° and, in particular, is 50°. About 80 to 120 recesses 21 or 22 are provided per cm$^2$ of plate area in the base plate 1 or 10 and the recesses 21, 22 are preferably produced by laser drilling. The recesses 21 and/or 22 extend through 60 to 90%, particularly 75% of the thickness of the base plate 1 or 10, which may be about 0.3 mm. The recesses 21 and 22 have a length of about 0.3 mm in the direction of their centre axes.

Figure 7:
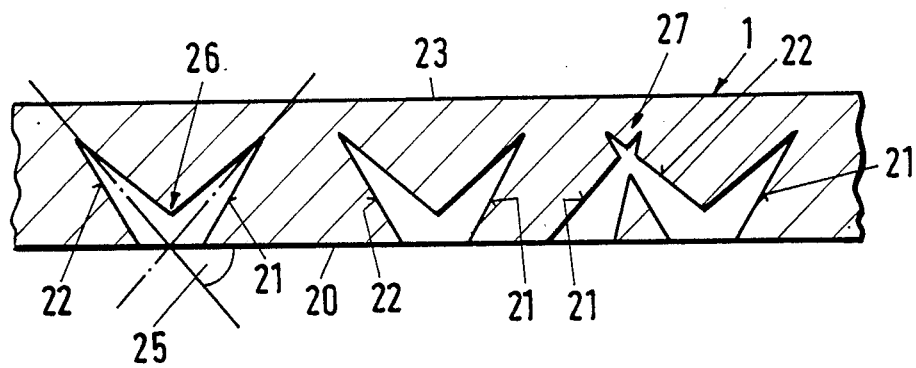
FIGS. 7 to 9 show broken away sectional illustrations substantially on the line A-B in FIG. 1 to illustrate different formations of the recesses forming the retention means in a base plate for an orthodontic device according to the present invention.
Figure 8:
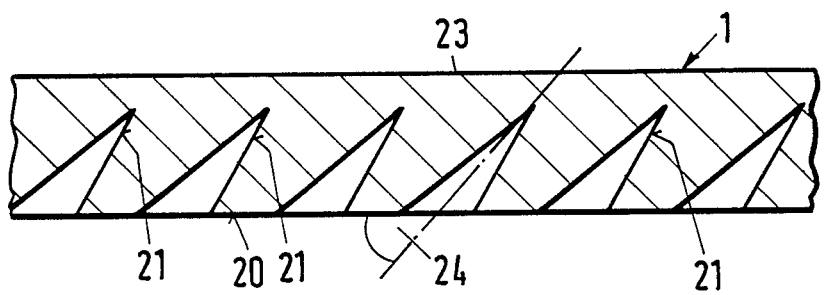
Figure 9:
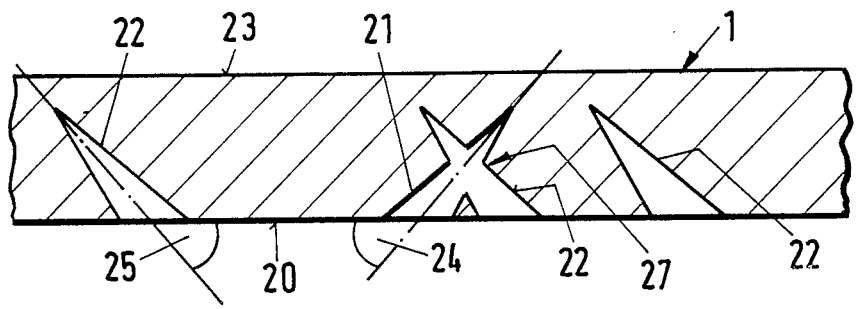

All the recesses may have a uniform alignment as is illustrated for the recesses 21 in FIG. 8, for example they may be inclined towards the right as in FIG. 8. The recesses 21 and 22, may, however, also be aligned differently, in groups, as the various illustrations in FIGS. 7 and 9 make clear. As can be seen from FIGS. 7 and 9, two or more recesses 21 and 22 may be combined to form groups 26, 27 which are different from one another. In the group 26, the point of intersection of the centre axes of recesses 21, 22 which are different from one another lies in the plane of the underside 20 of the base plate 1, while in the groups 27, the point of intersection of the centre axes of recesses 21 and 22 which are different from one another is situated in the vicinity of the apices of the cones. The intersections may be so situated that all the recesses inside the base plate 1 or 10 are interlaced.

This facilitates filling the recesses with an adhesive which is introduced for the direct adhesion of the base plate to the surface of a tooth and, after hardening, connects the bracket firmly to the tooth, the recesses 21, 22 forming reliable retention means as a result of their strong undercutting.

In its form as an adhesive support or adhesive base, the base plate 1 or 10 can also be used in conjunction with other bracket designs and there replace the foil layer and the gauze layer, for example.

I claim:

1. An orthodontic device in the form of a bracket comprising wings disposed on a baseplate, welding means welding said wings to said baseplate, said baseplate being formed as a separate preformed individual part, said wings being formed as separate shaped parts which are individually cut out in final shape from a bar by laser cutting, said baseplate having one side to which said wings are welded and an opposite side defining a base side, and a plurality of recesses in said base side formed by a laser beam, said recessed having a conical configuration with one end being the apex and the other end being circular, said circular end opening up onto said base side, said recesses having a longitudinal axis extending through said apex and through the center of said circular end, said apex extending at an acute angle relative to said base side.

2. An orthodontic device according to claim 1, wherein said wings have a frontal rounded surface with one end portion of said surface defining a sloping foot section which approaches said one side of said baseplate at an acute angle.

3. An orthodontic device according to claim 2, wherein said welding means welds said sloping wing foot section to said one side of said baseplate.

4. An orthodontic device according to claim 1, wherein said welding means comprises fusion welds without a welding agent utilizing laser welding.

5. An orthodontic device according to claim 1, wherein said acute angle is from 40-60 degrees.

6. An orthodontic device according to claim 5, wherein said acute angle is about 50 degrees.

7. An orthodontic device according to claim 1, wherein said baseplate has 50-120 recesses per square centimeter area of said base side.

8. An orthodontic device according to claim 1, wherein at least some of said recesses have axes which intersect axes of other recesses.

9. An orthodontic device according to claim 8, wherein said intersection occurs in the plane of said base side of said baseplate.

10. An orthodontic device according to claim 8, wherein said intersection occurs closer to said cone apex than to said open end of said recesses.

11. An orthodontic device according to claim 1, wherein said recesses extend to a depth of from 60-90% of the thickness of said baseplate.

12. An orthodontic device according to claim 11, wherein said recesses extend to a depth of about 75% of the thickness of said baseplate.

13. An orthodontic device according to claim 1, wherein the axes of at least some recesses are non-parallel to the axes of other of said recesses.

* * * * *